United States Patent [19]

Rotman

[11] Patent Number: 4,734,372

[45] Date of Patent: * Mar. 29, 1988

[54] CELL CULTURING METHODS AND APPARATUS

[75] Inventor: M. Boris Rotman, Jamestown, R.I.

[73] Assignee: Brown University Research Foundation, Providence, R.I.

[*] Notice: The portion of the term of this patent subsequent to Dec. 17, 2002 has been disclaimed.

[21] Appl. No.: 623,183

[22] Filed: Jun. 21, 1984

Related U.S. Application Data

[63] Continuation-in-part of Ser. No. 463,669, Feb. 4, 1983.

[51] Int. Cl.$^4$ ............... C12Q 1/29; C12Q 3/00
[52] U.S. Cl. .................. 435/291; 435/287; 435/4; 435/29; 436/4; 436/34; 422/48; 422/61; 422/68
[58] Field of Search ............... 435/3, 4, 29, 32, 34, 435/240, 241, 284, 287, 291, 808, 810, 811; 436/4, 34, 63, 68, 172, 178; 422/48, 61, 68

[56] References Cited

U.S. PATENT DOCUMENTS

| | | | |
|---|---|---|---|
| 2,942,520 | 6/1960 | Rose | 435/284 |
| 3,691,017 | 9/1972 | Brown et al. | 435/287 |
| 3,726,597 | 4/1973 | Duorak et al. | 435/284 |
| 3,821,087 | 6/1974 | Knazek et al. . | |
| 3,883,393 | 5/1975 | Knazek et al. . | |
| 3,928,142 | 12/1975 | Smith | 435/287 |
| 4,184,922 | 1/1980 | Knazek et al. . | |
| 4,201,845 | 5/1980 | Feder et al. . | |
| 4,220,725 | 9/1980 | Knazek et al. . | |
| 4,241,187 | 12/1980 | White . | |
| 4,242,459 | 12/1980 | Chick et al. | 435/284 |
| 4,308,351 | 12/1981 | Leighton et al. . | |
| 4,391,912 | 7/1983 | Yoshida et al. | 435/284 |
| 4,440,853 | 4/1984 | Michaels et al. | 435/284 |
| 4,537,860 | 8/1985 | Tolbert et al. | 435/284 |

FOREIGN PATENT DOCUMENTS

| | | |
|---|---|---|
| 2319204 | 12/1979 | Fed. Rep. of Germany . |
| 0916373 | 1/1963 | United Kingdom . |
| 0901266 | 1/1982 | U.S.S.R. ............ 435/284 |

OTHER PUBLICATIONS

Maeda, Hiroshi et al., "Investigation of Factors Involved in the Uptake Velocity of Fluorescein Diacetate and Intracellular Fluorescence Polarization Value. II Cytotoxicity Produced by Anticancer Agents. Cell Structure and Function. 7, (2), pp. 177-182, (Jun. 1982).
Tsuda et al., *Cell Structure and Function*, vol. 7, pp. 165-175, (1982).

*Primary Examiner*—Samuel Scott
*Assistant Examiner*—H. A. Odar
*Attorney, Agent, or Firm*—Thomas J. Engellenner

[57] ABSTRACT

A system and protocol for performing cytotoxicity studies including apparatus and methods for culturing the biopsied cells, for providing oxygenated nutrients, for removing cell-waste products, for introducing a fluorogenic substrate, for introducing cytotoxic agents including anticancer drugs, for measuring the released fluorescence and for measuring intracellular accumulation of fluorescein. Cytotoxicity can be determined by measuring fluorescence in the efflux of the vessel and concommitantly by direct photometric comparisons of the cells in the vessel before and after exposure to the cytotoxic agent.

14 Claims, 8 Drawing Figures

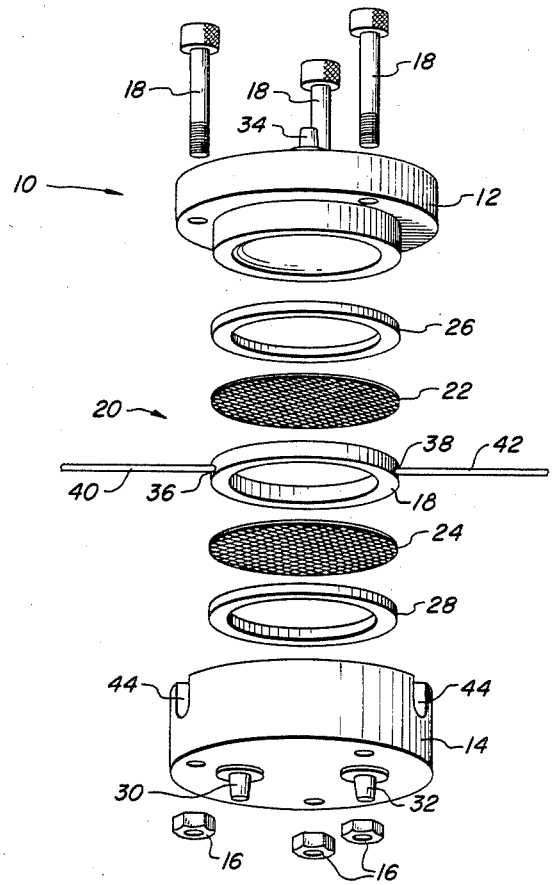
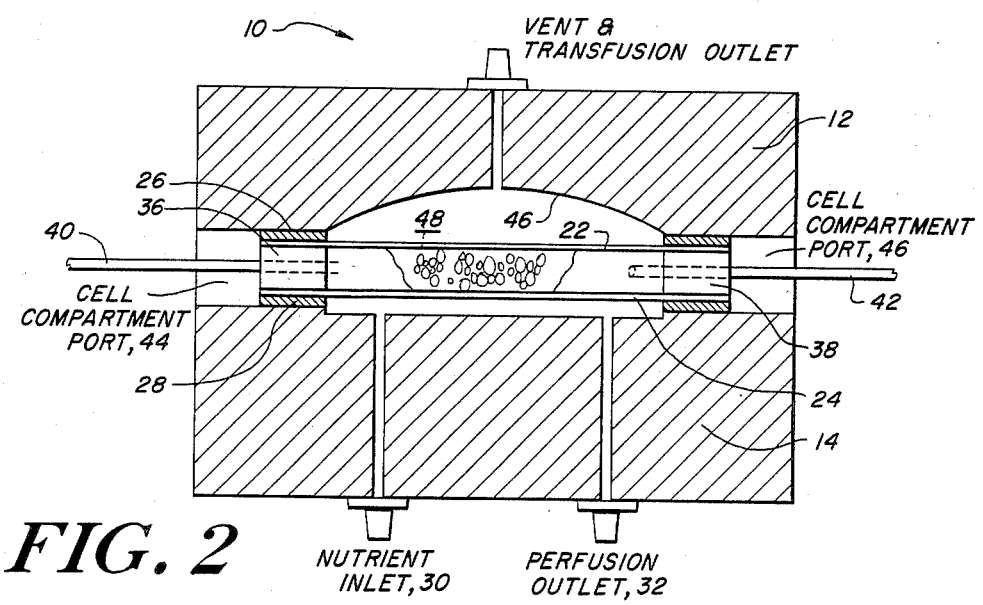

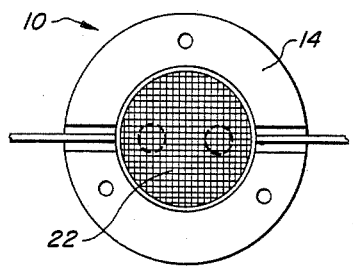
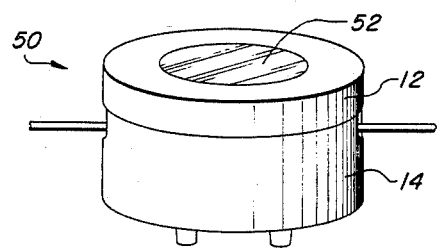
FIG. 3  FIG. 4
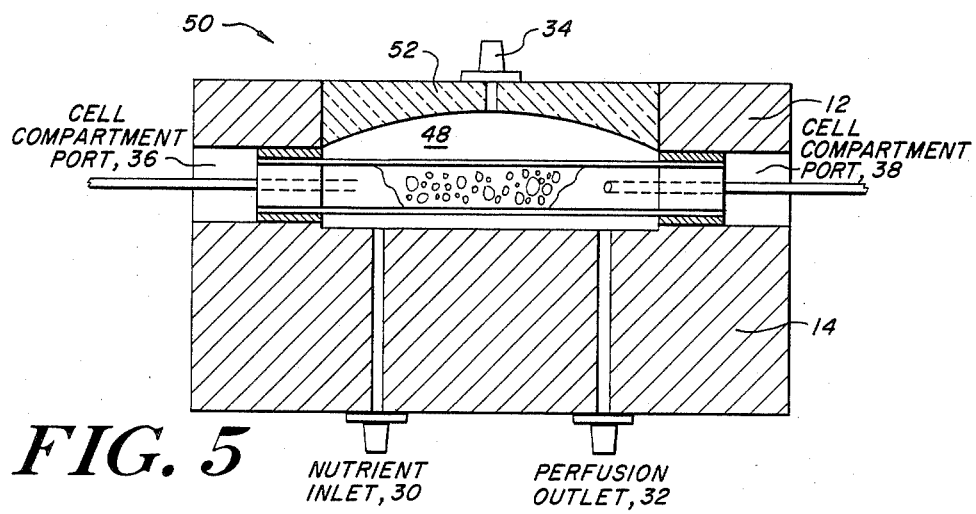
FIG. 5
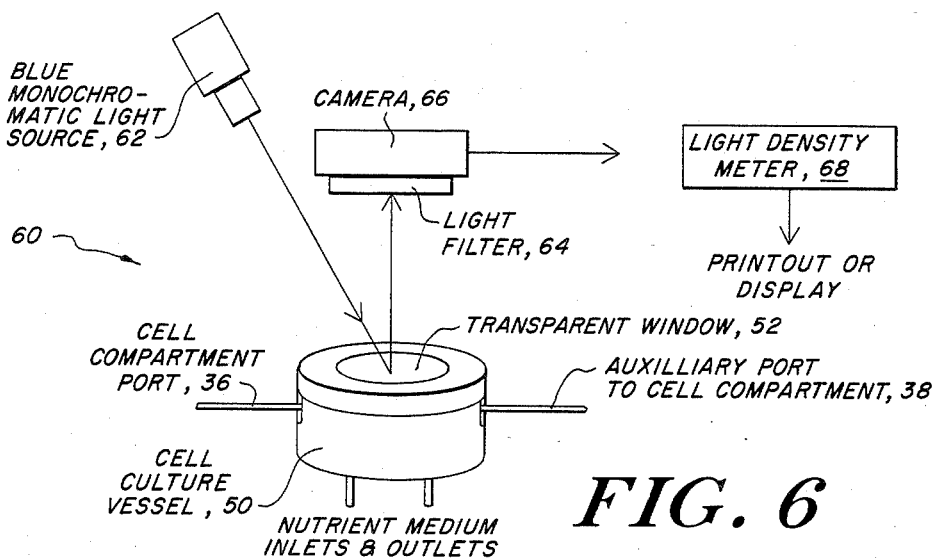
FIG. 6

CONTROL TUMOR WITHOUT TREATMENT

TUMOR TREATED WITH ADRIAMYCIN FOR FIVE DAYS

CELL CULTURING METHODS AND APPARATUS

BACKGROUND OF THE INVENTION

This application is a continuation-in-part of U.S. patent application Ser. No. 463,669 filed Feb. 4, 1983, entitled "Cytotoxicity Assays in Artificial Organs", the disclosure of which is hereby incorporated by reference.

The technical field of this invention is cell culturing and, in particular, methods and apparatus for conducting cytotoxicity assays on biopsied cells. It is known that cancerous or otherwise abnormal cells of identical histopathological type show a wide range of responsiveness to particular drug therapies among individual patients. Predictive techniques, similar to the culture and sensitivity assays used for the management of microbial infections, would be of great assistance in selecting effective chemotherapy for individual cases.

Without individualized anti-cancer drug regimens, practitioners are forced to rely on past experience or reports on similar cell disorders or trial-and-error procedures. With the increasing number of anti-cancer agents available and the limited time often available for modifying doses or agents, the task of selecting the optimal regimen, without the aid of predictive assays, is very difficult.

A number of predictive systems have been proposed. See, for example, Salmon et al., "Quantitation of Differential Sensitivity of Human Stem Cells to Anti-cancer Drugs," Vol. 298 New England Journal of Medicine pp. 1321–1327 (1978). Typically, the prior art techniques involve the cloning of single cell suspensions from biopsy specimens in soft agar after brief exposure to particular anti-cancer drugs. See also, Buick et al., "Development of an Agar-Methyl Cellulose Clonogenic Assay for Cells in Transitional Cell Carcinoma of the Human Bladder," Vol. 39 Cancer Research pp. 5051–5056 (1979) and Von Hoff et al., "Direct Cloning of Human Malignant Melanoma in Soft Agar Culture," Vol. 50 Cancer pp. 695–701 (1982), for further details on agar culture techniques.

Various difficulties limit the usefulness of agar culture studies for predicting the effectiveness of cytotoxic agents against abnormal cells. Only a small fraction of biopsied cancer cells grow in soft agar. For example, when cell suspensions from myeloma specimens are plated in agar, plating efficiencies of 1:1000 are not uncommon. Thus, for statistically significant results comparing different drugs at different doses, large numbers of cells are required. In practice, only 60% of the patients have tumors large enough to be assayed. It is also not certain that colonies formed in agar will be derived from the most malignant tumor cells. Moreover, agar techniques typically limit drug exposure to a relatively brief period (i.e., one hour) prior to plating while the cell is suspended in a physiological solution. Hence, neither the exposure technique nor the subsequent growth in agar accurately mimic in vivo conditions. Additionally, the time required for evaluation is long (i.e., 14 to 30 days) compared to the often urgent need to establish a protocol for therapy. Finally, measurements of drug sensitivity by counting cell colonies can be subjective, statistically inaccurate and time consuming.

Another predictive system which has been proposed for chemotherapy studies involves the use of cell cultures grown in an artificial organ made of a matrix of synthetic capillaries. Quartles et al., "Hemodialysis-Matrix Perfusion Culture System: A New Technique for Studying Chemotherapeutic Activity Tumor Cells," Vol. 16 In Vitro 246 (1980), report the effect of one anti-cancer agent on tumor cells grown in an artificial capillary system. Following exposure to the drug, the cultured cells were removed from the capillary matrix and assayed for total and viable cells, as well as colony forming ability and growth in soft agar. For a review of capillary cultures, generally, see Schratter, "Cell Culture with Synthetic Capillaries," Vol. XIV Methods in Cell Biology pp. 95–103 (1976).

The capillary technique for studying chemotherapeutic activity reported by Quartles, supra, is subject to many of the same problems that limit the usefulness of agar studies. Quartles and his co-workers had to remove the cells from the capillary system in order to count total and viable cells. In practice, removing cells without damage from a capillary matrix is an ardent task. Typically, the cells are removed from the capillary matrix by enzyme treatment but this treatment can be more effective on dead cells than on living cells and quantitative results are difficult to obtain. Moreover, the culture is lost after enzyme treatment and cannot be used again.

Additionally, capillary systems also suffer from a need for large quantities of tumor cells. Typically, assays using capillary systems required on the order of 5 million cells per vessel. To perform a concurrent battery of cytotoxicity assays, a half dozen or more capillary vessels (i.e., 30 million cells) must be employed. Obtaining sufficient tumor cells for these purposes from biopsy samples directly is not possible and hence an analyst wishing to undertake a comprehensive toxicity study must first grow the biopsy sample into a larger colony. Growing such a colony or colonies may not be feasible or can take months, severely hampering any predictive use of the assay.

Accordingly, there exists a need for better apparatus and methods for performing cytotoxicity assays. An assay apparatus that would operate on smaller-sized samples, for example, on the order of 100,000 cells or less, and accurately predict cytotoxicity, would find practical use as a predictive measure of drug sensitivity and would satisfy a long-felt need in the field of cancer treatment.

Moreover, a predictive culture system should be easily inoculated and cell growth as well as drug exposure should mimic closely the human environment. Also importantly, the drug sensitivity should be quantifiable by a simple and accurate method in a relatively short time and preferably in a way that would permit a clinician to obtain a reading on the effectiveness of a particular agent without destruction of the culture so that the effects of a multi-step protocol (i.e., varying in agents or doses) can be measured sequentially.

In U.S. patent application Ser. No. 463,669, the present applicant has disclosed a simple, sensitive, cytotoxicity assay capable of widespread clinical application. In the method claimed therein the number of living cells in a culture vessel is evaluated by measuring the retention of fluorescein or a similar label by the cell membranes. In one preferred embodiment, the cultured cells are allowed to accumulate fluorescein through fluorochromasia, which occurs when a fluorogenic substrate, typically a nonpolar fluorogenic substrate such as an ester of fluorescein and an aliphatic acid, is introduced into a cell culture. The fluorogenic substrate penetrates the cell membranes where it is enzymatically hydrolyzed, liberating fluorescein and staining the cell brightly fluorescent under blue light. Since fluorescein, a negatively charged molecule, does not diffuse readily across the cytoplasmic membrane of normal cells, the process causes intracellular accumulation of fluorescein. However, when a dead cell is treated with the fluorogenic substrate, no intracellular accumulation of fluorescein is observed. Therefore, if the cells in the vessel have been killed by an agent prior to the introduction of a fluorescent substrate, hydrolysis of the substrate will not result in intracellular fluorescein accumulation.

SUMMARY OF THE INVENTION

The present application discloses a preferred design for a culture apparatus employing the method of U.S. patent application Ser. No. 463,669 as well as an improved protocol for its use. In one aspect the invention consists of a vessel including at least one cell growth surface and is preferably structured so that the vessel may be inoculated with undissociated fragments of biopsied tissues, thus retaining the basic cellular composition of the tumor (many tumors have been shown to exhibit cellular heterogeneity). The perfusion (diffusion and/or transfusion) of oxygen and nutrients combined with removal of cellular waste as well as the three-dimensional structure of the vessel make it likely that even tumor cells unable to grow in agar can be kept viable in the apparatus. Moreover, the sensitivity of fluorescence detection techniques allows the vessel to be employed with small numbers of cells, thus permitting simultaneous studies from even biopsy specimens of limited size, such as colon or lung cancer biposies.

In one preferred embodiment, the vessel is formed by an upper and a lower body element which are clamped together to form a shell defining a cavity for cell inoculation and nutrient circulation. The cells, themselves, are secured within the cavity by a cylindrical compartment bounded by an upper and a lower membrane, which are preferrably a porous material such as fibrous interwoven cellulose or a polymeric mesh. The cell compartment, membranes and shell can be sealed together by O-ring gaskets. Ports for cell inoculation and fluid passage also are disposed within the vessel.

In another aspect, the invention encompasses a system and protocol for performing cytotoxicity studies including apparatus and methods for culturing the biopsied cells, for providing oxygenated nutrients, for introducing a fluorogenic substrate, for introducing anti-cancer agents and for measuring the released fluorescence. Cytotoxicity can be determined by measuring fluorescence in the efflux of the vessel and also by direct photometric comparisons of the cells in the vessel before and after exposure to the anti-cancer agent.

In one preferred method, the biopsy sample is mechanically teased into smaller fragments and suspended in a medium to separate most of the normal cells from the malignant cells. The tumor cells can be further purified by density gradient centrifuging.

The tumor aggregates are then inoculated into the vessel and, after culturing in the vessel with nutrient medium, the fluorogenic substrate is introduced and the resulting fluorescein is allowed to accumulate. Once a steady state condition is reached, the excess substrate is removed and normal nutrient perfusion continues. The therapeutic agent to be tested can then be introduced into the cell compartment (directly or by perfusion) and the effluent monitored for a period of time (i.e., about 15 minutes to 2 hours) for changes in the amount of fluorescein released. With agents exhibiting delayed (i.e., radiomimetic) effects, more detailed records of the kinetics and fluorescence of the cell culture or its efflux can be obtained following each of a series of perfusions with fluorogenic substrate. Different fluorogenic substrates and temperature shifting can be employed to obtain more rapid or slower results.

Alternatively, the vessel can be constructed with a transparent viewing port and changes in fluorescence measured directly by photometric analysis. In one illustrated embodiment, the cell compartment is illuminated by monochromatic light and then photographed through a matching light filter to capture only the fluorescence of the living cells. The optical density of the photograph negative provides a simple, accurate measure of the intracellular fluorescein and, therefore, a parameter for cytotoxic effects of the agent being tested.

The methods disclosed herein permit the clinician to test the effects of prolonged exposure, different combinations and programmed schedules of drugs. Additionally, if a drug gives a negative cytotoxicity test, the vessel and culture can be recycled for subsequent drug testing.

The various therapeutic or chemical agents which can be tested according to the invention for effectiveness on individual cell cultures include: adriamycins, mitomycins, actinomycins, neomycins, vincristine, vinblastine, chlorambucil, cis-platinum, 6-mercapto purine, methotrexate, cyclophosphamide, melphalen, carmustine, methyl ester DOPA, BCNU, DTIC, 5-fluoruracil, m-AMSA, mitoxantrone, methyl GAG, acivicin, thymidine, hormones, antibodies, prostaglandins and lymphokines as well as X-rays or other agents as they become available.

The invention will next be described in connection with certain preferred embodiments; however, it should be clear that various changes and modifications can be made without departing from the spirit and scope of the claims. For example, a wide variety of commercially available growth media from companies such as Gibco Corporation and others may be employed as nutrients. These media are sold under names such as Dulbecco's Modified Eagle Medium (DMEM), Roswell Park Medium (RPMI) and Minimal Eagle Medium (MEM) and typically consist of amino acids, salts, vitamins, blood serum and other nutrients. Alternatively, in clinical applications, it may be preferred to use serum from the biopsied patient for all or part of the growth medium in order to further mimic in vivo exposure to the agents undergoing testing. Other additions can include x-irradiated feeder cells from autologous or heterologous origin, soft agar, and plasma clots.

Moreover, while a primary objective of this invention is to present methods and apparatus for predicting the responsiveness of cancer cells to chemotherapeutic agents, other uses may also prove valuable. For examples, drugs against other cell abnormalities can be tested and the methods and apparatus can also be used in assessing the effects of drugs on non-cancerous cells as a measure of the side-effects that a particular course of chemotherapy would cause in the patient.

BRIEF DESCRIPTION OF THE DRAWINGS

FIG. 1 is an exploded perspective view of a cell culturing apparatus according to the present invention.

FIG. 2 is a schematic side cross-sectional view of the apparatus of FIG. 1.

FIG. 3 is a schematic top cross-sectional view of the apparatus of FIG. 1.

FIG. 4 is a perspective view of an alternative embodiment of a cell culturing apparatus according to the present invention.

FIG. 5 is a schematic side cross-sectional view of the apparatus of FIG. 4.

FIG. 6 is a schematic drawing of a cytotoxicity assay system employing the apparatus of FIG. 4.

DETAILED DESCRIPTION OF THE PREFERRED EMBODIMENTS

Figure 7A:
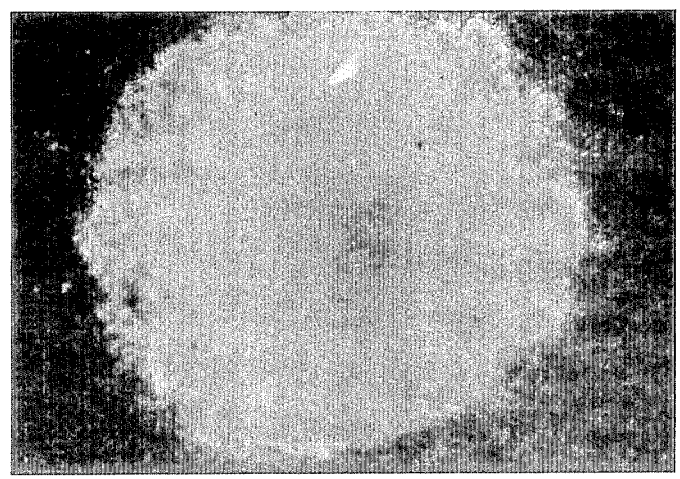
FIGS. 7a and 7b are photographs showing assay results.

In FIG. 1 a culture vessel 10 according to the present invention is shown having an upper shell element 12 and a lower shell element 14 adapted to be clamped together by nuts 16 and bolts 18. Within the cavity of the shell elements 12, 14, a cell compartment 20 is formed by a hollow cylindrical element 18 and porous upper and lower membranes 22, 24, respectively. The edges of the membranes 22, 24, and the hollow cylindrical element 18 are sealed to the shell by upper and lower elastomeric O-ring gaskets 26, 28, respectively.

As shown in FIG. 1 and in more detail in the cross-sectional view of FIG. 2, inlet 30 and outlet 32 in the lower shell element 14 permit the passage of nutrient-carrying fluids into and out of the cavity. Outlet 34 in the upper shell element permits venting of air from the cavity and can also serve as an alternate outlet for the nutrient medium. Ports 36 and 38 in the hollow cylindrical element 18 are connected to tubes 40 and 42, respectively which pass through slots 44 in the lower shell element 14 when the vessel 10 is clamped together. The ports 36, 38 serve as direct access points to the cell compartment 20 and are typically covered by septum plugs (not shown) when not in use. The upper surface 46 of the cavity 48 is preferably concave or conical to aid in venting.

A top cross-sectional view of the vessel 10 is presented in FIG. 3 showing the upper membrane 22 which defines the top of the cell compartment 20. In one preferred embodiment, the porous membrane 22 can be matted or woven fibrous cellulose, such as the material from which tea bags are made. Alternatively, filter paper or synthetic meshes such as woven nylon, cellulose acetate or silicon polycarbonate may be employed. The pore size can range from about 5 to about 35 microns, preferably 10-30 microns and most preferably about 15-25 microns, when non-disassociated biopsy fragments are used for inoculation. However, when single cell suspensions are used, a smaller pore size is preferred, for example, on the order of 5 microns or less. When synthetic meshes are employed as the membranes 22, 24 in vessel 10 it can be advantageous to coat the membranes with a material such as agar, collagen, fibronectin or gelatin and/or soak them overnight in serum before assembly to ensure better compatibility with the inoculated biopsy cells. Nutrient perfusion is accomplished by a peristaltic pump or gravity flow.

FIGS. 4 and 5 show an alternative culture vessel 50 according to the present invention having a transparent viewing window 52 in the upper shell element 12. As seen in the cross-sectional view of FIG. 5, vessel 50 has a structure similar to vessel 10 of FIGS. 1-3, including an upper and lower shell element 12, 14 defining a cavity 48 within which is nested a cell compartment 20 formed by hollow cylinder 18, membranes 22, 24 and gaskets 26, 28. Inlet 30, outlets 32, 34 and port 36, 38 are essentially identical in structure to the same-numbered elements in FIGS. 1-2 and perform the same functions.

Figure 7B:
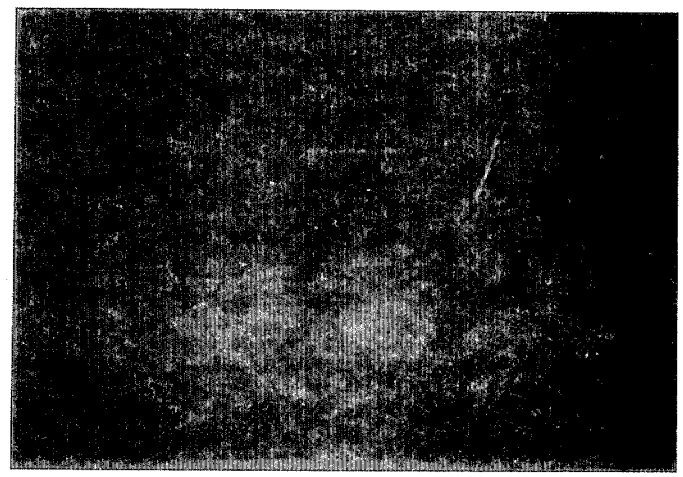

In FIG. 6 a system 60 employing the vessel of FIGS. 4-5 is shown having a light source 62, preferably of blue monochromatic light, which illuminates vessel 50 through window 52. Light from the vessel 50 passes through filter 64, which is preferably a matching blue filter and absorbs the blue wavelengths while passing only the greenish fluorescent light. The fluorescence is captured by camera 66 mounted on a low-power microscope and processed by light density meter 68 to yield cell viability measurements at each step of the assay procedure. Camera 66 may take still photographs, the negatives of which are analysed by the light density meter 68, or alternatively, camera 66 and meter 68 may be formed as a high speed video scanning and electronic processing device for fully-automated operations. FIGS. 7a and 7b show the results of an assay employing the system of FIG. 6. In addition, computer scanning of photographs provides parameters with which to evaluate objectively cell proliferation or death.

A typical protocol for conducting a cytotoxicity assay in accordance with the present invention begins with the straining of a biopsy sample through a 16 gauge stainless steel mesh to obtain suitable fragments for inoculation into the vessel. Enzyme extraction and single cell suspensions need not be employed. The straining process can be repeated as necessary until sample fragments roughly on the order of 0.2 mm$^3$ are obtained.

The fragments are then decanted in a medium, such as RPM1-1640 medium, for about 5 minutes at 0° C. wherein non-aggregated normal cells (i.e., red blood cells, lymphocytes, macrophages) will form a supernatant suspension while the aggregates of malignant cells can be collected in a sediment layer. The decantation procedure is repeated two more times. Typically, the deposited material comprises about 80–90% tumor cells. The sedimented cell fragments can be further purified, if desired, by layering the cell suspension on a solution of albumin or similar specific gravity carbohydrate solution and centrifuging, for example at about 20–300 × G for about 5 minutes. Under these conditions, the purified tumor cell aggregates separate at the interface and can be drawn off the solution.

The biopsy fragments are mixed again with a medium, such as the RPMI medium, and inoculated into the cell compartment 20 of vessel 10 or 50 via a syringe through the septum plug on one or the other port 36, 38. Inside the cell compartment membranes 22, 24 (typically filter paper of interlaced cellulose fibers with pore sizes of roughly 20 microns on the average) secures the tumor aggregates within the compartment while providing passageways for the nutrient medium to diffuse through the vessel.

After an appropriate culturing period (typically 1–10 days) the fluorescent substrate can be applied either by injection directly into the cell compartment through one or both ports or, preferably, by mixture into the circulating medium. (The fluorogenic substrate can be substituted for the calf serum in the medium). Exposure to the substrate typically lasts from about 15 minutes to 2 hours, preferably one-half hour at room temperature.

After exposure, the circulating medium containing the substrate is replaced with a new medium, preferably including a serum component. There is normally no need to wash the cell compartment to remove excess substrate. The vessel effluent or cell compartment, itself, is then examined to detect fluorescence levels and thereby determine the status of the cells. This procedure can be repeated daily to determine long-term effects. An adjustment period of about 24 hours is preferred before introducing the therapeutical agent to be tested.

The therapeutic agent is typically introduced by adding it to the circulating medium thereby mimicking the method by which the patient would be exposed. Following exposure another adjustment period of about 24 hours is preferred before the culture is again exposed to the fluorogenic substrate.

Additions, subtractions and modifications of the above-described preferred embodiments will be apparent to those skilled in the art and are within the scope of the following claims.

I claim:

1. A cytotoxicity assay system comprising a cell culturing vessel having a cell enclosure into which cells can be introduced and cultured;

nutrient-transporting means for transporting nutrients to the cells, the nutrient-transporting means include a source of nutrients and at least one fluid permeable membrane, connecting said source of nutrients to said cells, across which nutrients can migrate to nourish the cells within the vessel;

fluorogenic substrate-transporting means for transporting a fluorogenic substrate to the cell compartment, so that living cells within the vessel will take up said substrate and accumulate a characteristic fluorescence;

means for introducing a therapeutic agent into the cell compartment; and means for measuring cytotoxicity within the cell compartment, including means for detected changes in the fluorescence of the cells within the vessel.

2. The system of claim 1 wherein the vessel further includes at least one transparent surface through which fluorescence within the cell enclosure can be observed.

3. The system of claim 1 wherein the vessel further includes at least one sampling port for withdrawing an sample from the cell enclosure to measure the fluorescence of the sample.

4. The system of claim 1 wherein the fluid permeable membrane has a pore size ranging from about 5 to about 35 microns.

5. The system of claim 1 wherein the fluid permeable membrane is a synthetic capillary.

6. The system of claim 1 wherein the fluid permeable membrane is a fibrous cellulose material.

7. The system of claim 1 wherein the permeable membrane is polymeric mesh.

8. The system of claim 1 wherein the means for measuring fluorescence is a camera.

9. The system of claim 8 wherein the means for measuring fluorescence further includes a monochromatic light source and a matched filter.

10. A method of assaying the sensitivity of biopsied cells to therapeutic agents, the method comprising:
a. culturing the cells in a vessel;
b. contacting the cells with a fluorogenic substrate whereby living cells accumulate a characteristic amount of fluorescence;
c. introducing the agent into the vessel; and
d. measuring changes in the fluorescence by photometrically analyzing the intensity of fluorescence within the vessel as an indicator of the sensitivity of the cells to the agent.

11. The method of claim 10 wherein the step of measuring changes in fluorescence further including photometrically recording the fluorescence with a photographic camera.

12. The method of claim 10 wherein the step of measuring changes in fluorescence further includes photometrically recording the fluorescence with a video camera.

13. The method of claim 10 wherein the step of measuring changes in fluorescence further includes illuminating the cultured cells with blue monochromatic light.

14. The method of claim 13 wherein the step of measuring changes in fluorescence further includes filtering light from the cultured cells with a matching blue filter.

* * * * *